(12) United States Patent
Davis et al.

(10) Patent No.: US 11,305,225 B2
(45) Date of Patent: Apr. 19, 2022

(54) APPARATUS FOR COLLECTING PARTICLES WITHIN A FLUID

(71) Applicant: NOKIA TECHNOLOGIES OY, Espoo (FI)

(72) Inventors: Ian Davis, Dublin (IE); Kevin Nolan, Dublin (IE)

(73) Assignee: NOKIA TECHNOLOGIES OY, Espoo (FI)

( * ) Notice: Subject to any disclaimer, the term of this patent is extended or adjusted under 35 U.S.C. 154(b) by 116 days.

(21) Appl. No.: 16/225,226

(22) Filed: Dec. 19, 2018

(65) Prior Publication Data

US 2019/0184326 A1 Jun. 20, 2019

(30) Foreign Application Priority Data

Dec. 20, 2017 (EP) ..................................... 17208838

(51) Int. Cl.
| | | |
|---|---|---|
| *B01D 49/00* | (2006.01) | |
| *B01J 19/10* | (2006.01) | |
| *B06B 1/06* | (2006.01) | |
| *G01N 1/40* | (2006.01) | |
| *G01N 21/35* | (2014.01) | |
| *G01N 21/84* | (2006.01) | |
| *H04R 17/10* | (2006.01) | |

(Continued)

(52) U.S. Cl.
CPC ......... *B01D 49/006* (2013.01); *A61M 11/001* (2014.02); *A61M 15/001* (2014.02); *A61M 15/0003* (2014.02); *B01D 21/283* (2013.01); *B01J 19/10* (2013.01); *B06B 1/06* (2013.01); *G01N 1/4077* (2013.01); *G01N 21/1717* (2013.01); *G01N 21/35* (2013.01); *G01N 21/84* (2013.01); *H04R 17/10* (2013.01); *A61M 11/005* (2013.01); *A61M 15/0085* (2013.01); *A61M 2205/3306* (2013.01); *A61M 2205/3313* (2013.01); *G01N 2001/4094* (2013.01)

(58) Field of Classification Search
None
See application file for complete search history.

(56) References Cited

U.S. PATENT DOCUMENTS

| | | | | |
|---|---|---|---|---|
| 4,983,189 A | * | 1/1991 | Peterson | A61M 1/36 |
| | | | | 210/188 |
| 5,085,783 A | * | 2/1992 | Feke | B01D 21/283 |
| | | | | 210/243 |

(Continued)

FOREIGN PATENT DOCUMENTS

| | | |
|---|---|---|
| CA | 2 953 939 A1 | 1/2016 |
| WO | 2016053181 A1 | 4/2016 |

OTHER PUBLICATIONS

European Office Action issued in corresponding European Patent Application No. 17 208 838 7-1010 dated Jun. 17, 2021.

*Primary Examiner* — Christopher P Jones
*Assistant Examiner* — Brit E. Anbacht
(74) *Attorney, Agent, or Firm* — Squire Patton Boggs (US) LLP

(57) ABSTRACT

An apparatus includes a chamber and an intake device configured to control a flow of fluid into the chamber. The fluid comprises particles; a resonance device is configured to resonate the chamber to provide an acoustic standing wave within the chambers. The frequency of the standing wave is selected to cause particles above a specific size to collect at a node of the standing wave.

18 Claims, 6 Drawing Sheets

Figure 1:
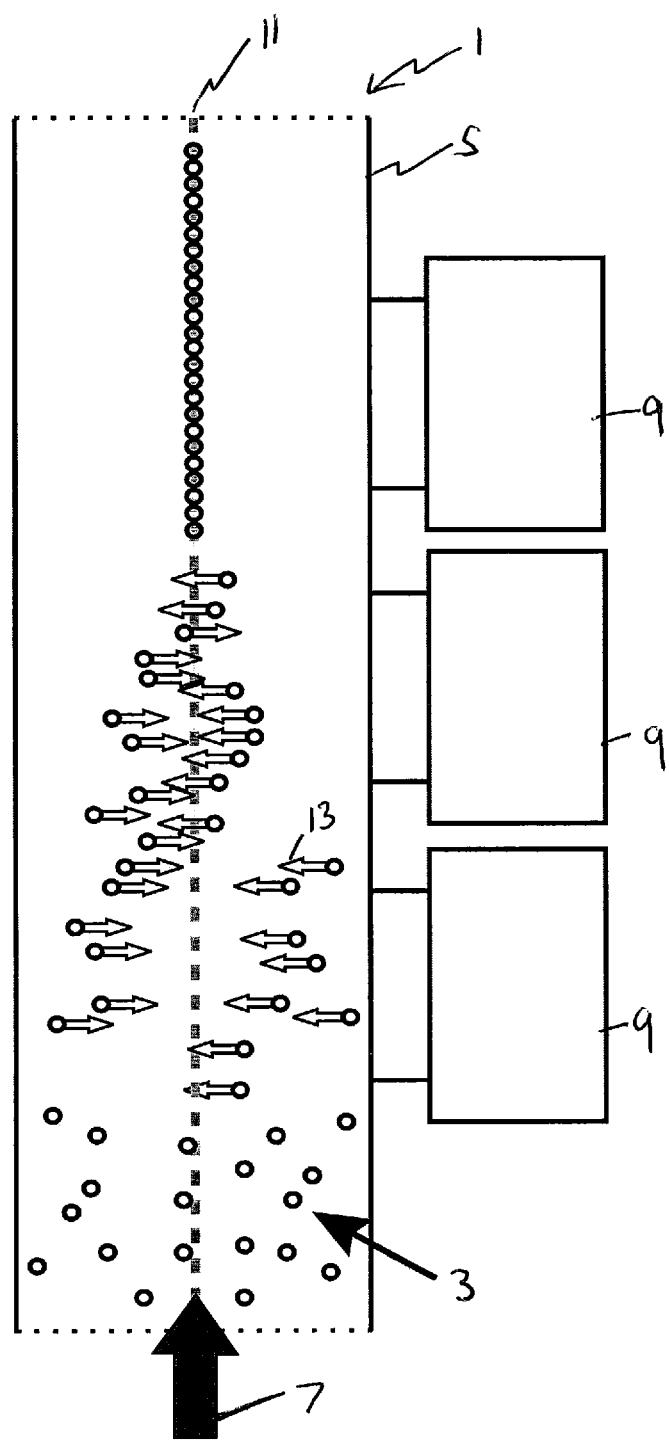

(51) Int. Cl.
  *G01N 21/17* (2006.01)
  *A61M 15/00* (2006.01)
  *B01D 21/28* (2006.01)
  *A61M 11/00* (2006.01)

(56) References Cited

U.S. PATENT DOCUMENTS

| | | | | |
|---|---|---|---|---|
| 5,225,089 A * | 7/1993 | Benes | ................ | B01D 21/283 210/188 |
| 6,221,258 B1 * | 4/2001 | Feke | ................ | B01D 21/0012 210/748.05 |
| 9,533,241 B2 | 1/2017 | Presz, Jr. et al. | | |
| 2008/0245745 A1 * | 10/2008 | Ward | ................ | G01N 1/4077 209/590 |
| 2010/0078384 A1 * | 4/2010 | Yang | ................ | G01N 33/491 210/645 |
| 2011/0123392 A1 * | 5/2011 | Dionne | ................ | C01B 13/10 422/1 |
| 2011/0278218 A1 | 11/2011 | Dionne et al. | | |
| 2012/0086938 A1 | 4/2012 | Folkenberg | | |
| 2014/0011240 A1 * | 1/2014 | Lipkens | ................ | H01L 41/053 435/71.1 |
| 2015/0017678 A1 * | 1/2015 | Matula | ................ | B01L 3/502784 435/30 |
| 2015/0125948 A1 * | 5/2015 | Lipkens | ................ | A61M 1/3678 435/308.1 |
| 2015/0191716 A1 * | 7/2015 | Lipkens | ................ | B01D 21/283 435/173.9 |
| 2015/0321129 A1 * | 11/2015 | Lipkens | ................ | B01D 43/00 210/748.05 |
| 2016/0002070 A1 * | 1/2016 | Lipkens | ................ | B01D 21/0045 422/128 |
| 2016/0089620 A1 * | 3/2016 | Lipkens | ................ | B06B 1/0644 435/173.9 |
| 2016/0237394 A1 * | 8/2016 | Lipkens | ................ | C12M 29/10 |
| 2016/0319270 A1 * | 11/2016 | Lipkens | ................ | A61M 1/3678 |
| 2016/0339360 A1 * | 11/2016 | Lipkens | ................ | B01D 17/00 |
| 2016/0361670 A1 * | 12/2016 | Lipkens | ................ | B01D 21/0045 |
| 2016/0363579 A1 * | 12/2016 | Gilmanshin | ................ | B01L 3/502761 |
| 2016/0369236 A1 * | 12/2016 | Kennedy, III | ................ | C12M 29/04 |
| 2017/0008029 A1 * | 1/2017 | Lipkens | ................ | B06B 3/04 |
| 2017/0088809 A1 * | 3/2017 | Lipkens | ................ | B06B 1/0223 |
| 2017/0128857 A1 * | 5/2017 | Lipkens | ................ | B06B 1/0276 |
| 2017/0137774 A1 * | 5/2017 | Lipkens | ................ | B06B 1/0644 |
| 2017/0159005 A1 * | 6/2017 | Lipkens | ................ | B06B 1/0644 |
| 2017/0191022 A1 * | 7/2017 | Lipkens | ................ | C12M 47/02 |
| 2017/0267991 A1 * | 9/2017 | Lipkens | ................ | B06B 1/0644 |
| 2017/0291122 A1 * | 10/2017 | Lipkens | ................ | H04R 1/06 |
| 2017/0298316 A1 * | 10/2017 | Kennedy, III | ................ | C12M 29/04 |
| 2017/0304746 A1 * | 10/2017 | Lipkens | ................ | B01D 17/02 |
| 2017/0355623 A1 * | 12/2017 | Lipkens | ................ | C02F 1/52 |
| 2018/0207551 A1 * | 7/2018 | Lipkens | ................ | B01D 21/283 |
| 2018/0290089 A1 * | 10/2018 | Vincent | ................ | B01D 43/00 |
| 2018/0296954 A1 * | 10/2018 | Trampler | ................ | C12M 47/12 |
| 2018/0298323 A1 * | 10/2018 | Lipkens | ................ | B01D 21/2411 |
| 2019/0184326 A1 * | 6/2019 | Davis | ................ | G01N 21/35 |
| 2019/0191252 A1 * | 6/2019 | Lipkens | ................ | B01D 21/28 |
| 2020/0017376 A1 * | 1/2020 | Dionne | ................ | C02F 1/36 |

* cited by examiner

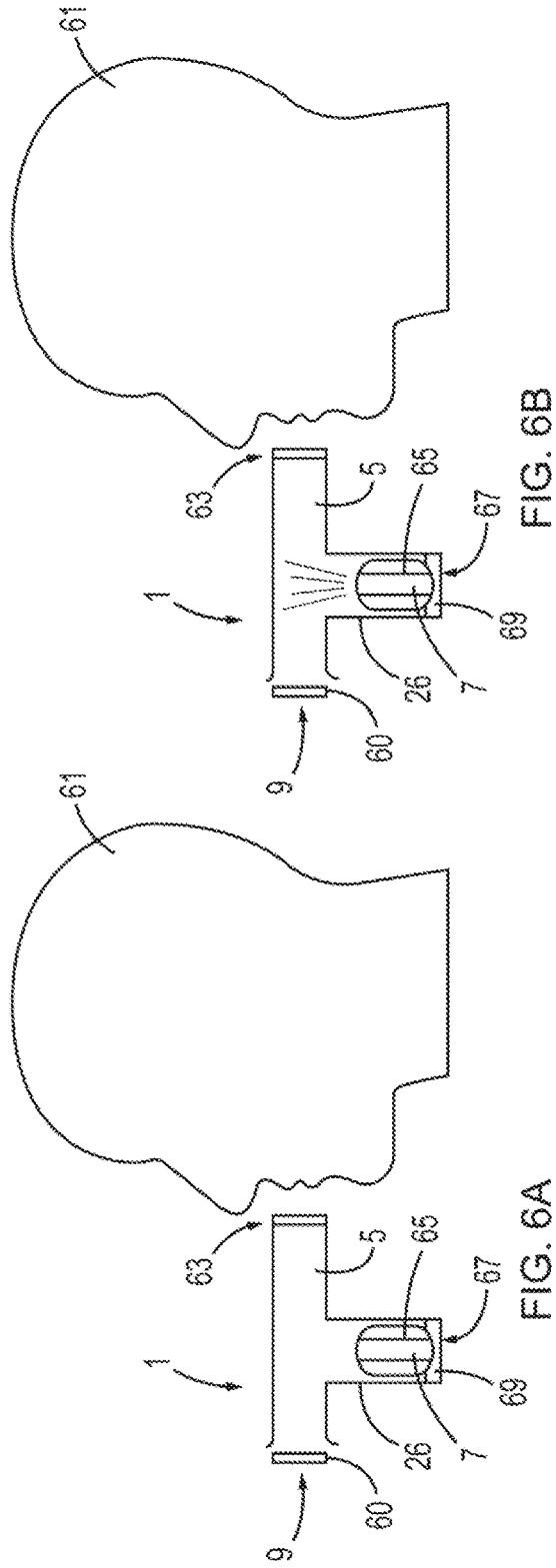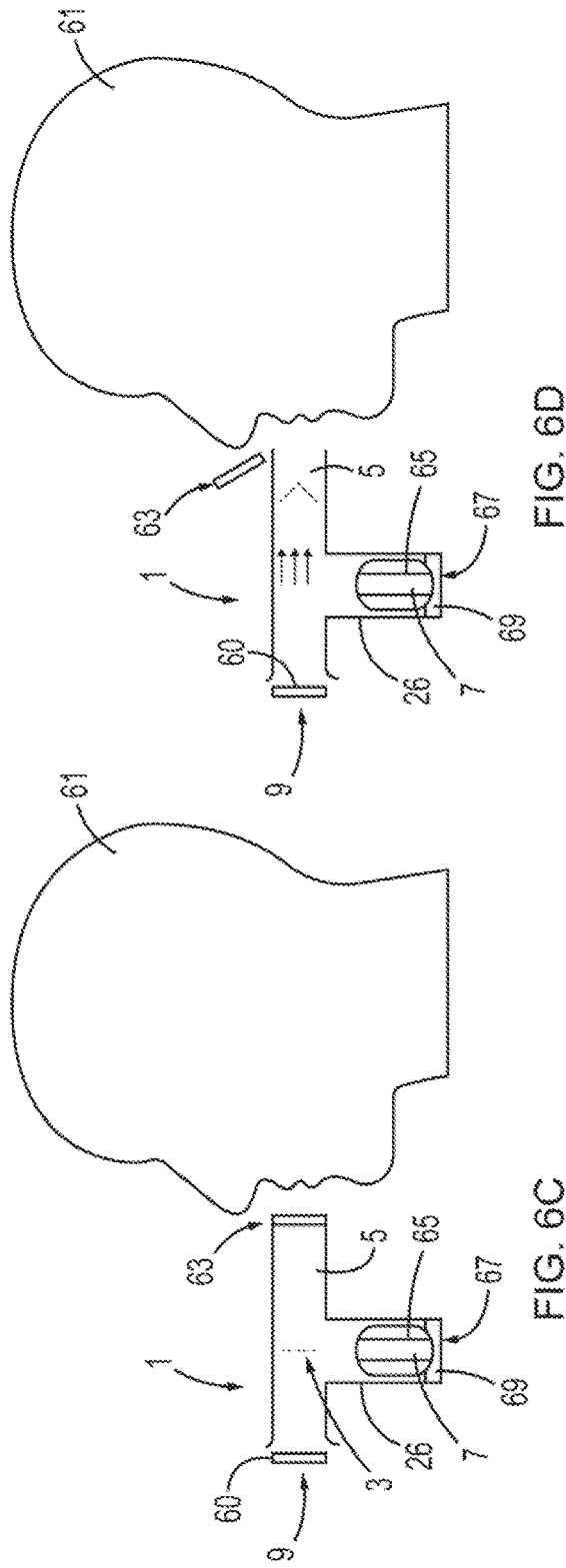

APPARATUS FOR COLLECTING PARTICLES WITHIN A FLUID

TECHNOLOGICAL FIELD

Examples of the disclosure relate to an apparatus for collecting particles within a fluid. In some examples of the disclosure the apparatus could be used to determine the size of dust particles or to collect particles of a particular size for drug delivery.

BACKGROUND

It can be useful to know the size of particles within a fluid in many different applications. For example where electronic components are stored in shelf units it is useful to try to limit the amount of dust which gets into these units as the dust can cause corrosion and affect the cooling of the components. By detecting the size of dust particles in the air around the components filters can be provided to effectively filter out particles of that size.

Also, it is well know that the particle size of drugs or other medicaments affects how well they are absorbed when they are inhaled by a user. The size of a particle affects the depth with which the drug is absorbed into the respiratory system. Therefore a user or a medical practitioner may want to select particles of a specific size so that they are absorbed by a specific part of the respiratory system.

Therefore it is useful in many applications to enable particles of a particular size to be collected.

BRIEF SUMMARY

According to various, but not necessarily all, examples of the disclosure, there is provided an apparatus comprising: a chamber; intake device configured to control a flow of fluid into the chamber, wherein the fluid comprises particles; a resonance device configured to resonate the chamber to provide an acoustic standing wave within the chamber; and wherein the frequency of the standing wave is selected to cause particles above a specific size to collect at a node of the standing wave.

The particles may be suspended within the fluid.

The fluid may comprise a gas.

The intake device may comprise at least one of, a piezoelectric transducer, a fan, a heating element, an aerosolizer.

The resonance device may comprise one or more piezoelectric transducers.

The apparatus may comprise a detection device configured to detect the particles collected at the node of the standing wave. The detection device may comprise one or more light sources and one or more photodetectors. The one or more light sources may be configured to provide light of a plurality of different wavelengths and the one or more photodetectors may be arranged to enable the response of the particles to the different wavelengths of light to be detected.

The detection device may comprise an imaging device.

The chamber may comprise a sealing device configured to seal the chamber.

The sealing device may be configured to be removed to enable the fluid and particles to be removed from the chamber.

The apparatus may comprise a reservoir arranged to collect particles that have a size such that they do not collect at the node.

The particles above a specific size may have a diameter above a specific length.

The particles above a specific size may have a mass above a specific mass.

The particles may comprise one or more droplets.

According to various, but not necessarily all, examples of the disclosure, there is provided a drug delivery apparatus comprising an apparatus as described above.

According to various, but not necessarily all, examples of the disclosure, there is provided a dust detection apparatus comprising an apparatus as described above.

According to various, but not necessarily all, examples of the disclosure, there is provided a method of treating a medical condition comprising: controlling a flow of fluid into a chamber of an apparatus, wherein the fluid comprises particles; resonating the chamber to provide an acoustic standing wave within the chamber, wherein the frequency of the standing wave is selected to cause particles above a specific size to collect at a node of the standing wave; and delivering the particles collected at the node to a subject.

The method may comprise selecting the frequency of the standing wave to control the size of particles collected at the node of the standing wave.

According to various, but not necessarily all, examples of the disclosure, there is provided an apparatus comprising: a chamber; an intake arranged to controlling a flow of fluid into the chamber, wherein the fluid comprises particles; one or more resonators arranged to resonate the chamber to provide an acoustic standing wave within the chamber; and wherein the frequency of the standing wave is selected to cause particles above a specific size to collect at a node of the standing wave.

According to various, but not necessarily all, embodiments of the invention there is provided examples as claimed in the appended claims.

BRIEF DESCRIPTION

For a better understanding of various examples that are useful for understanding the detailed description, reference will now be made by way of example only to the accompanying drawings in which:

FIG. 1 illustrates an apparatus;

FIG. 2 illustrates an apparatus;

FIGS. 3A to 3D illustrate an example apparatus in use;

FIG. 4 illustrates an apparatus;

FIGS. 5A to 5C illustrate an example apparatus in use;

FIGS. 6A to 6D illustrate an example apparatus in use in a drug delivery system; and FIG. 7 illustrates an example method of using an apparatus.

DETAILED DESCRIPTION

Examples of the disclosure relate to an apparatus 1 which enables particles that are suspended within a fluid and have a particular size to be collected. Examples of the disclosure use standing acoustic waves to enable the particles 3 to be collected at specific locations with a chamber 5. The frequency of the standing acoustic waves can be tuned so that particles 3 having a particular size are collected at a node of the standing wave. Once the particles 3 have been collected they could be analysed to enable the parameters of the particles 3 to be determined. For example the quantity and type of particles 3 could be analysed. In some examples, once the particles 3 have been detected they can be provided to a user for a specific purpose, for example, for drug delivery.

FIG. 1 schematically illustrates an apparatus 1 according to examples of the disclosure. The apparatus 1 comprises a chamber 5, an intake device or means 7 for controlling a flow of fluid into the chamber 5 and a resonance device or means 9 for resonating the chamber 5 to provide an acoustic standing wave within the chamber 5.

The chamber 5 comprises an enclosed volume or partially enclosed volume within which fluid can be received. In some examples the chamber 5 may be sealed. In other examples the chamber 5 could be open ended.

In the example of FIG. 1 the chamber 5 comprises a cylindrical tube. Other shapes for the chamber 5 could be used in other examples of the disclosure, for example the tube could be rectangular. In the example of FIG. 1 the chamber 5 is arranged to extend towards a vertical direction. In other examples the chamber 5 could extend towards a horizontal direction or any other suitable direction.

In the example of FIG. 1 the chamber 5 is an open ended chamber. In other examples one or both of the ends of the chamber 5 could be closed.

The intake means 7 could comprise any means which may be arranged to control a flow of fluid into the chamber 5. The intake means 7 may be arranged to cause movement of the fluid so that at least some of the fluid is drawn into the chamber 5. In some examples the intake means 7 could be arranged to control the rate at which the fluid is taken into the chamber 5.

In some examples the intake means 7 could comprise a fan which may be arranged to draw fluid into the chamber 5. In some examples the intake means 7 could comprise means which do not comprise any moveable parts. For example the intake means 7 could comprise one or more heating elements which may be arranged to heat the fluid and so enable the fluid to be drawn into the chamber 5.

In some examples the intake means 7 could comprise one or more piezoelectric transducers. The piezoelectric transducers could be arranged to cause movement of the fluid to drive the fluid into the chamber 5. The piezoelectric transducers of the intake means 7 may be provided in addition to any piezoelectric transducers of the resonance means 9. The piezoelectric transducers of the intake means 7 may be provided at a different location of the chamber 5 to any piezoelectric transducers of the resonance means 9. For instance, in the example of FIG. 1 the piezoelectric transducers of the intake means 7 would be provided at the lower end of the chamber 5 while the piezoelectric transducers of the resonance means 9 are provided at the side of the chamber 5.

In other examples the intake means 7 could comprise an aerosolizer. The aerosolizer may be arranged to spray a fluid that comprises particles 3 into the chamber 5.

Figure 2:
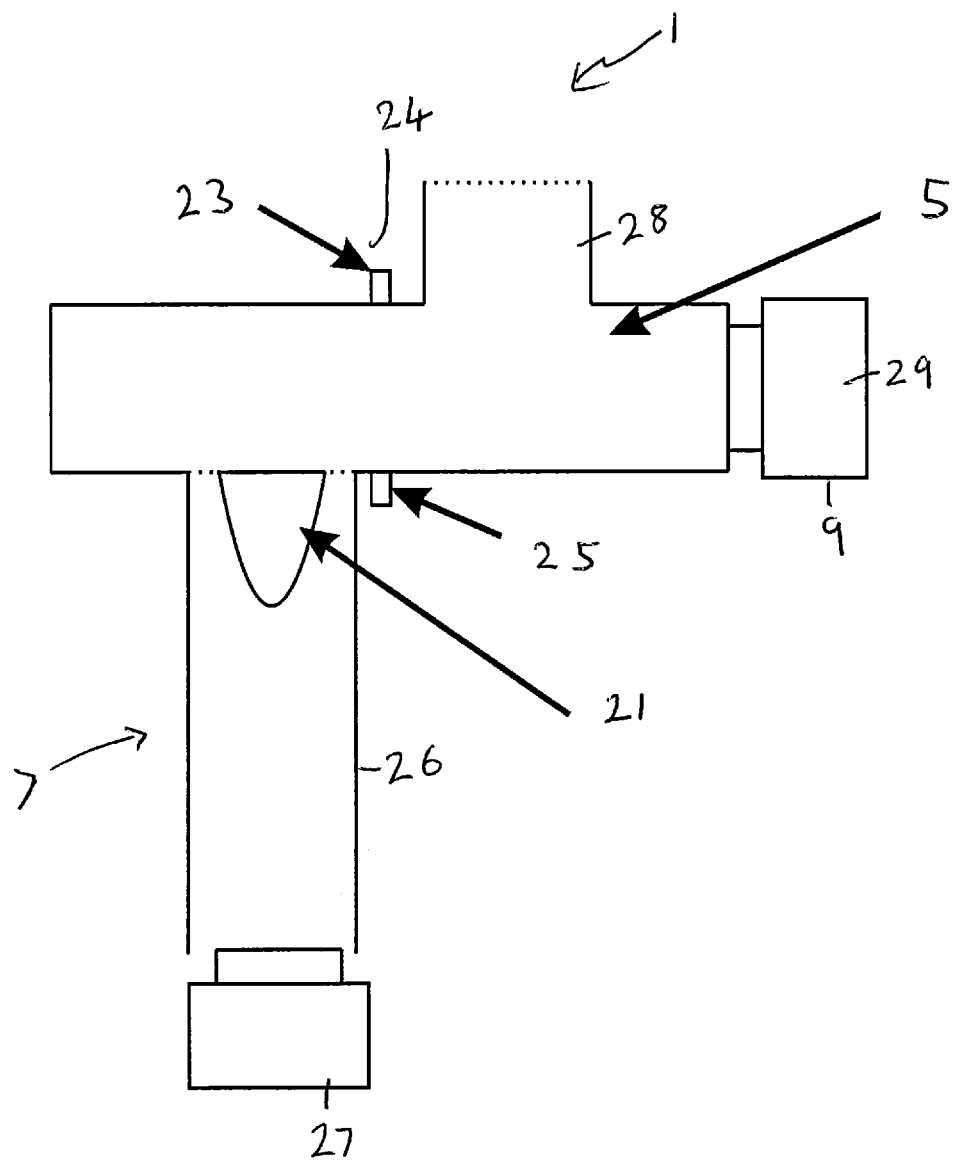

The fluid that is drawn into the chamber 5 by the intake means 7 could comprise any suitable fluid. In some examples the fluid may comprise any fluid that comprises the environment within which the apparatus 1 is located. In other examples the fluid could comprise a fluid that is stored within a reservoir of the apparatus 1.

In some examples the fluid could comprise a gas such as air. The fluid may comprise particles 3. The particles 3 may be suspended within the fluid. The type of fluid that is used and the type of particles 3 that are suspended within the fluid may depend on the application of the apparatus 1. For example where the apparatus 1 is used to detect dust particle size the fluid that is taken into the chamber 5 could comprise air with suspended dust particles 3. Where the apparatus 1 is used for drug delivery the fluid that is taken into the chamber 5 could comprise a gas comprising a plurality of medicinal particles 3 suspended within the gas.

In some examples of the disclosure the particles 3 may comprise solid particles. For instance, the particles 3 could comprise dust particles, a solid medicine or any other suitable type of solid. In some examples of the disclosure the particles 3 could comprise liquid particles. In such examples the particles 3 may comprise one or more droplets. The liquid particles could comprise a liquid medicine, water droplets or any other suitable type of liquid.

The resonance means 9 may comprise any means for exciting the chamber 5 to provide an acoustic standing wave within the chamber 5. In some examples the resonance means 9 may be arranged to provide an ultrasonic standing wave within the chamber 5. The resonance means may comprise one or more resonators.

In some examples the resonance means 9 may comprise one or more piezoelectric transducers. In the example of FIG. 1 the resonance means 9 comprises three piezoelectric transducers provided along the length of the chamber 5. it is to be appreciated that any number of piezoelectric transducers could be provided in other examples of the disclosure and that these piezoelectric transducers could be provided at any suitable location within or adjacent to the chamber 5.

The resonance means 9 are arranged to provide a standing wave within the chamber 5. In the example of FIG. 1 a node 11 of the standing wave is located at the centre of the chamber 5, as indicated by the dashed line. The acoustic standing wave acts to drive particles 3 having a size above a specific size towards the node 11.

In some examples the size could be a diameter of the particles 3. In such examples particles 3 having a size above a specific size may comprise particles 3 having a diameter above a specific length. In some examples the size could be a mass of the particles 3. In such examples particles 3 having a size above a specific size may comprise particles 3 having a mass above a specific mass.

As shown in FIG. 1 when the fluid initially enters the chamber 5, at the lower end of the chamber 5, the particles 3 are evenly distributed throughout the fluid. As the fluid moves through the chamber 5 and the acoustic standing pressure wave pushes the particles 3 towards the node 11 of the standing wave. In the example of FIG. 1 this causes the particles 3 to move towards the centre of the chamber 5 as indicated by the arrows 13. When the fluid reaches the top of the chamber 5 the particles 3 are collected in the centre of the chamber 5. The collected particles 3 can then be analysed or used as required.

In some examples of the disclosure the size of the particles 3 that are collected at the node 11 may depend on the ratio of the diameter of the particles 3 to the wavelength of the acoustic standing wave. By using different wavelengths to create the standing wave, different sized particles 3 can be collected.

Other factors may affect the size of particles 3 that are collected at the node 11 of the standing wave, in addition to the particle size and wavelength of the standing wave. For example, the compressibility of the particles 3 may affect the forces driving the particles towards the node 11. The ratio of the compressibility of the particles 3 to the compressibility of the fluid may affect the size of the particles 3 that are collected at the node 11 because incompressible particles 3 may be affected by the acoustic standing wave more than compressible particles 3.

FIG. 2 schematically illustrates an example apparatus 1 that can be used to detect sizes of particles 3. For example the apparatus 1 could be used to detect the size of dust particles 3, water droplets or other unwanted particles 3. The information about the size of the particles 3 could be used to enable a more effective particle filter to be provided.

In the example of FIG. 2 the chamber 5 comprises a tube. The tube may be cylindrical or any other suitable shape. The chamber 5 is arranged horizontally in FIG. 2. The chamber 5 could be arranged in other configurations in other examples of the disclosure.

In the example of FIG. 2 the intake means 7 comprises a first piezoelectric transducer 27 and a conduit 26.

The first piezoelectric transducer 27 is arranged at an open end of the conduit 26 so that actuation of the first piezoelectric transducer 27 causes the fluid to be drawn into the conduit 26. It is to be appreciated that other means for enabling the fluid to be drawn into the conduit 26 could be used in other examples of the disclosure. For example the means could comprise one or more fans or heating elements or any other suitable components. In some examples the means could comprise an ultrasonic acoustic source which could be arranged to induce bulk motion of the fluid via dissipation of high frequency noise into the fluid. In such examples the same piezoelectric transducer could be used for both the intake means 7 and the resonance means 9.

The conduit 26 extends between the first piezoelectric transducer 27 and the chamber 5 so that fluid drawn into the conduit 26 is provided to the chamber 3. The conduit 26 may be arranged to separate the first piezoelectric transducer 27 from the chamber 5 so that acoustic waves generated by the first piezoelectric transducer 27 do not interfere with any standing acoustic waves in the chamber 5.

In the example of FIG. 2 an absorptive material 21 is provided within the conduit 26 between the first piezoelectric transducer 27 and the chamber 5. The absorptive material 21 is arranged to absorb any acoustic waves from the first piezoelectric transducer 27 and prevent these acoustic waves from being transmitted into the chamber 5 and interfering with any standing waves within the chamber 5. The absorptive material 21 could comprise any suitable type of material which may be arranged to absorb acoustic waves generated by the first piezoelectric transducer 27. In some examples the absorptive material 21 could comprise an acoustic foam with a small particle size or any other suitable type of material. It is to be appreciated that examples where the intake means 7 comprises a fan or a heating element the absorptive material 21 might not be needed.

In the example of FIG. 2 the conduit 26 extends perpendicularly from a side of the chamber 5. The conduit 26 could be provided in a different position in other examples of the disclosure.

The resonance means 9 comprises a second piezoelectric transducer 29. The second piezoelectric transducer 29 is provided at an end of the chamber 5. The second piezoelectric transducer 29 is arranged to oscillate so as to create an acoustic standing wave within the chamber 5. The second piezoelectric transducer 29 may be arranged to oscillate at different frequencies to enable standing waves having different frequencies to be generated within the chamber 5.

The apparatus 1 also comprises detection means 24. The detection means 24 may comprise any means which enables the collected particles 3 to be detected. In some examples the detection means 24 may also enable the collected particles 3 to be analysed. This may enable the size, type or any other suitable parameter of the particles 3 to be determined.

In the example of FIG. 2 the detection means 24 comprises a light source 23 and a photodetector 25. The light source 23 may be arranged to provide a single wavelength of light or a band of wavelengths of light. For instance, in some examples the light source 23 may be arranged to provide infrared light. In other examples the light source 23 could be arranged to provide visible light. The light source 23 could comprise one or more light emitting diodes or any other suitable means.

The photodetector 25 could comprise any means which may be arranged to transduce incident light into an electrical output signals. The electrical output signal may be indicative of the amount of light that is incident on the photodetector 25.

The detection means 24 is arranged so that the light source 23 is provided on a first side of the chamber 5 and the photodetector 25 is provided on an opposite side of the chamber 5 so that the particles 3 collected within the chamber 3 block the path of the light between the light source 23 and the photodetector 25. This may enable the amount of light that is detected by the photodetector 25 to be used to determine the quantity of particles 3 within the fluid.

The detection means 24 may be provided at any suitable position along the length of the chamber 5. The detection means 24 may be provided in locations where a node of a standing wave will be established.

In the example of FIG. 2 only one detection means 24 is shown. It is to be appreciated that in other examples a plurality of detection means 24 provided at a plurality of locations along the length of the chamber 5 could be used.

In the example of FIG. 2 the apparatus 1 also comprises an exit conduit 28. The exit conduit 28 may comprise means which enables the fluids and particles to be removed from the chamber 5 once the particles have been analysed and/or measured. The exit conduit 28 extends perpendicularly from a side of the chamber 5. The exit conduit 28 could be provided on an opposing side of the chamber 5 to the conduit 26.

The example apparatus 1 as shown in FIG. 1 could be provided in a dust detection device, a moisture detection device or any other suitable type of device.

FIGS. 3A to 3D illustrate the example apparatus 1 of FIG. 2 in use. The apparatus 1 may be being used to enable the particles 3 in an environment to be analysed.

Figure 3A:
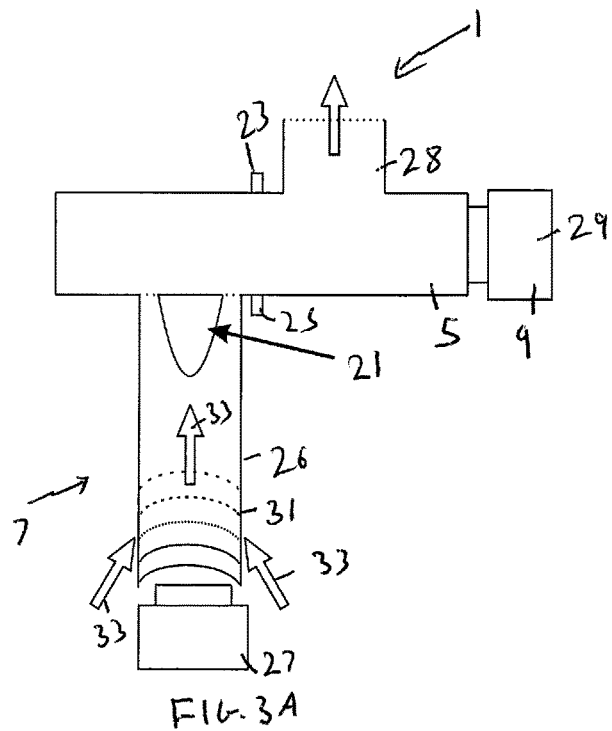

In FIG. 3A the intake means 7 are operated to enable fluid to be drawn into the conduit 26 and from the conduit 26 into the chamber 5. In the example of FIG. 3A the intake means 7 are operated by using the first piezoelectric transducer 27 to generate ultrasonic waves 31. In such examples the excitation of the first piezoelectric transducer 27 may be of the order of several MHz. The ultrasonic waves 31 draw the fluid into the conduit 26 as indicated by the arrows 33.

The fluid that is drawn into the chamber 5 may be representative of the fluid and particles 3 that are provided in the environment around the apparatus 1. This enables the apparatus 1 to be used to measure the dust content, or make any other analysis if the particles 3, within the environment.

Once the fluid has been drawn into the chamber 5 the intake means 7 is deactivated. Any means for moving the fluid is turned off to enable the fluid within the chamber 5 to reach a quiescent state. While the fluid within the chamber 5 is reaching the quiescent state neither the first piezoelectric transducer 27 in the intake means 7 nor the second piezoelectric transducer 29 in the resonance means 9 is activated.

Figure 3B:
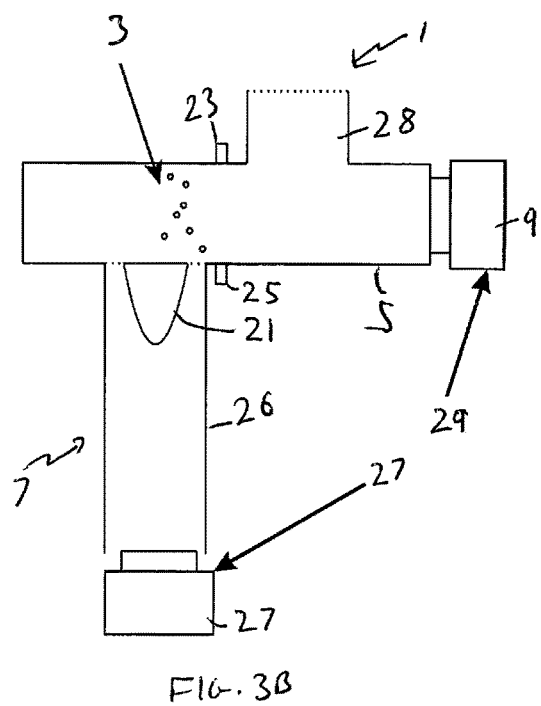

When the fluid is in a quiescent state the particles 3 within the fluid may be randomly dispersed within the chamber 5 as shown in FIG. 3B.

Figure 3C:
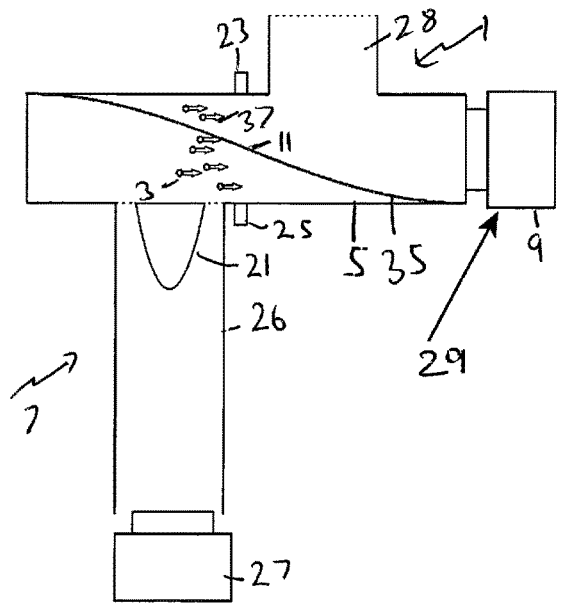

Once the fluid has reached the quiescent state, then as shown in FIG. 3C the second piezoelectric transducer 29 is activated. The resonant frequency of the second piezoelectric transducer 29 is matched to a longitudinal resonance frequency of the chamber 5 so that a standing acoustic wave is established within the chamber 5.

Figure 5A:
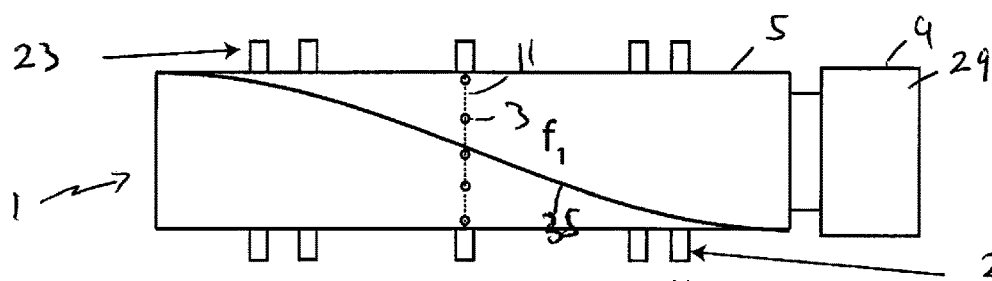
Figure 5B:
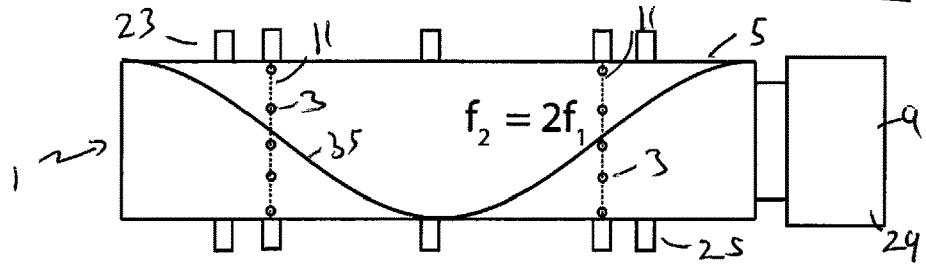
Figure 5C:
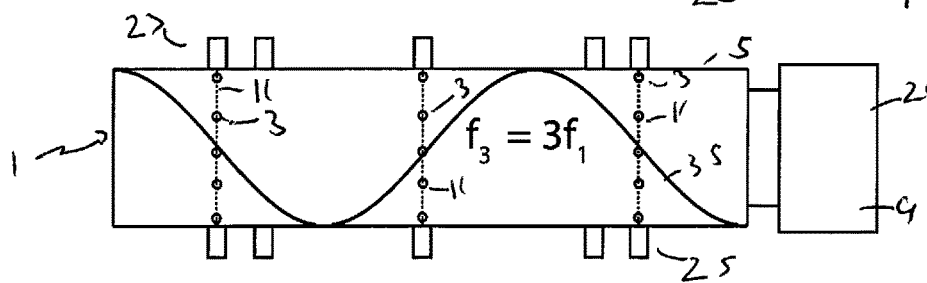

The acoustic wave 35 shown in FIG. 3C is an acoustic pressure wave. Antinodes of the pressure wave are created at the ends of the chamber 5. In the example of FIG. 3C the ends of the chamber 3 are closed so that antinodes of the pressure wave are always provided at the end of the end of chamber 5. The acoustic wave 35 shown in FIG. 3C is a first harmonic wave which has a single node 11 which is provided in the centre of the chamber 5. The same chamber 5 could be resonated at different frequencies as shown in FIGS. 5A to 5C.

The acoustic pressure forces the particles 3 within the fluid which have a diameter above a specific size towards the node 11 where the pressure is not changing as indicated by the arrows 37. The diameter of the particles 3 that are affected by the standing acoustic wave may be determined by the frequency of the standing acoustic wave.

Figure 3D:
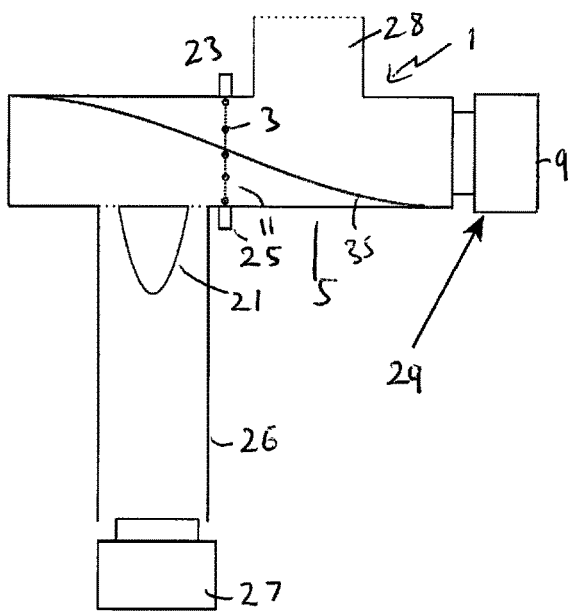

After the standing acoustic wave has been active for a sufficient period of time the particles 3 will collect at the node 11 as shown in FIG. 3D. In the example of FIG. 3D the particles 3 form a sheet or plane of particles 3 in the location of the node 11.

The detection means 24 is aligned with the position of the node 11 so that the sheet of particles 3 is positioned between the light source 23 and the photodetector 25. This enables the amount of particles 3 to be quantified by detecting the amount of light from the light source 23 which is incident on the photodetector 25.

In the example of FIGS. 3A to 3D the apparatus 1 is operated periodically so that the fluid is in a quiescent state before the standing wave is established. In other examples the apparatus 1 could be operated continuously. In such examples the intake means 7 and the resonance means 9 could be operated continuously rather than being deactivated periodically. Whether the apparatus 1 is operated periodically or continuously may depend on the application that the apparatus 1 is being used for.

Figure 4:
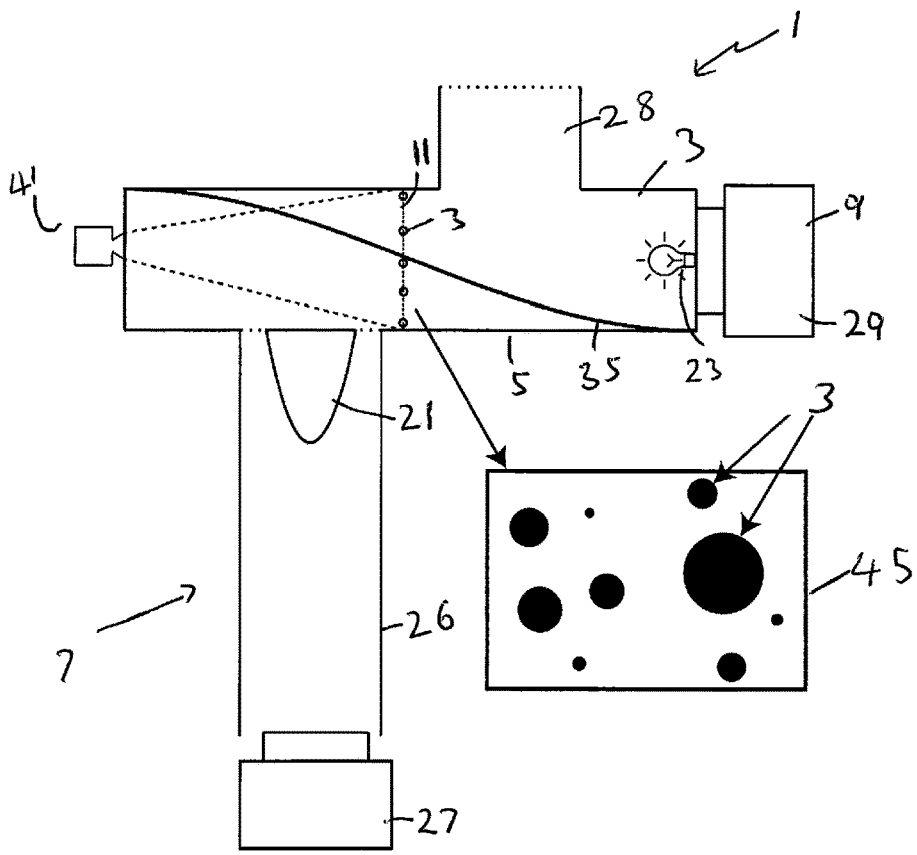

FIG. 4 illustrates another example apparatus 1. The example apparatus of FIG. 4 is similar to the example apparatus 1 shown in FIGS. 2 and 3A to 3D. However in the example of FIG. 4 the detection means 24 comprises an imaging device 41 rather than a light source 23 and photodetector 25. The chamber 5, intake means 7 and resonance means 9 may be as shown in FIGS. 2 and 3A to 3D. Corresponding reference numerals are used for corresponding features.

In the example apparatus 1 of FIG. 4 a light source 23 is provided at a first end of the chamber 5 and an imaging device 41 is provided at an opposite end of the chamber 5. In the example of FIG. 4 the light source 23 is provided at the same end of the chamber 5 as the resonance means 9 so that the imaging device 41 is provided at the opposite end of the chamber 5. In other examples the imaging device 41 could be provided at the same end of the chamber 5 as the resonance means 9 and the light source 3 could be provided at the opposite end.

The light source 23 may be arranged to provide a single wavelength of light or a band of wavelengths of light. For instance, in some examples the light source 23 may be arranged to provide infrared light. In other examples the light source 23 could be arranged to provide visible light. The light source 23 could comprise one or more light emitting diodes or any other suitable means.

The imaging device 41 could comprise a camera or any other suitable means. The imaging device 41 may comprise one or more image sensors. The image sensors may comprise any means which may be configured to convert an incident beam of light into an image. The image sensor may comprise means for converting an incident beam of light into an electrical signal which can then be converted into an image. The image sensor used in the imaging device 41 may comprise, for example, a digital CCD (charge coupled device) or a complementary metal-oxide-semiconductor (CMOS) sensor or any other suitable sensor.

The imaging device 41 may also comprise one or more optical arrangements. The optical arrangements may comprise any suitable optical devices which may be configured to focus an incident beam of light onto the image sensor. The optical arrangements may be arranged so that the field of view of the imaging device 41 is aligned with the position of the node 11 of the standing wave.

In some examples the optical arrangement of the imaging device 41 may be adjustable to enable focused images of different planes along the length of the chamber 5 to be obtained. This may enable focused images to be obtained when different frequencies of standing waves, and different positions of the nodes 11 are used. This may enable different sized particles 3 to be images and analysed using the imaging device 41.

FIG. 4 shows an example image 45 of the particles 3 that may be obtained by the imaging device 41. As the imaging device 41 is located perpendicular to the plane of particles 3 this enables an image of the different particles to be obtained. In some examples the image 45 can be analysed to categorize the size of the particles and the number of particles 3 within different size ranges. The categorization may be performed using image analysis processing circuitry or any other suitable means.

In some examples the detection means 24 may be arranged to provide information about the chemistry of the particles 3. For example the light source 23 may be arranged to provide light which could cause phosphorescence or fluorescence, or any other suitable phenomenon, of particles 3 comprising a particular chemical. The amount of phosphorescence or fluorescence that is detected by the photodetectors 24 may therefore give an indication of the chemistry of the particles 3.

It is to be appreciated that other factors could be used to analyse the particles 3. For instance the amount of reflection, refraction or absorption of particular wavelengths of light may be used to provide information about the chemistry of the particles 3.

FIGS. 5A to 5C illustrate another example apparatus 1 in use. The examples of FIGS. 5A to 5C show different resonant frequencies being used to generate the standing acoustic pressure wave. In the examples of FIGS. 5A to 5C the intake means 7 and the exit conduit 28 are not shown for clarity.

In the examples of FIGS. 5A to 5C the detection means 24 comprises an array of light sources 23 and an array of photodetectors 25.

The detection means 24 is arranged so that the array of light sources 23 is provided on a first side of the chamber 5 and the array of photodetectors 25 is provided on an opposite side of the chamber 5. The array of light sources 23 and the array of photodetectors 25 may be arranged so that each light source 23 has a corresponding photodetector 25 positioned on an opposing side of the chamber 5. Each pair of light source 23 and photodetector 25 may be positioned at the location of a node 11 of a standing wave of a particular frequency.

FIG. 5A shows the apparatus 1 when the second piezoelectric transducer 29 is resonating the chamber 5 at a first fundamental frequency $f_1$. At this fundamental frequency $f_1$ a single node 11 is provided within the standing acoustic pressure wave. This node 11 is located in the centre of the chamber 5 and will affect particles 3 having a diameter above a specific size.

When the apparatus 1 is operating in this fundamental frequency $f_1$ mode the particles 3 can be detected by a first light source 23 and a first photodetector 25 located at the centre of the chamber 5.

FIG. 5B shows the apparatus 1 when the second piezoelectric transducer 29 is resonating the chamber 5 at a second frequency $f_2$. This second frequency $f_2$ is equal to twice the fundamental frequency $f_1$. At this second frequency $f_2$ two nodes 11 are provided within the standing acoustic pressure wave. These nodes 11 are located towards the ends of the chamber 5 and will affect particles 3 having a diameter above a specific size where the specific size for the second frequency $f_2$ is smaller than the specific size for the fundamental frequency $f_1$.

When the apparatus 1 is operating in this second frequency $f_2$ mode the particles 3 can be detected by a pair of light sources 23 and a pair of photodetectors 25 where the light sources 23 and the photodetectors 25 located towards the ends of the chamber 5.

FIG. 5C shows the apparatus 1 when the second piezoelectric transducer 29 is resonating the chamber 5 at a third frequency $f_3$. This third frequency $f_3$ is equal to three times the fundamental frequency $f_1$. At this third frequency $f_3$ three nodes 11 are provided within the standing acoustic pressure wave. These nodes 11 comprise one node located in the centre of the chamber 3 and two located towards the ends of the chamber 5. The standing acoustic pressure wave will affect particles 3 having a diameter above a specific size where the specific size for the third frequency $f_3$ is smaller than the specific size for both the fundamental frequency $f_1$ and the second frequency $f_2$.

When the apparatus 1 is operating in this third frequency $f_3$ mode the particles 3 can be detected by a three light sources 23 and three corresponding photodetectors 25 where the light sources 23 and the photodetectors 25 located at the centre of the chamber 5 and towards the ends of the chamber 5.

The apparatus 1 may be operated in the different frequency modes at different times. This enables the particles 3 to be categorized by size because the different frequencies will affect different sized particles 3. The different sized particles 3 can then be detected by the different light sources 23 and photodetectors 25.

FIGS. 6A to 6D illustrate an example apparatus 1 in use in a drug delivery system.

The example apparatus 1 of FIGS. 6A to 6D comprises a chamber 5, an intake means 7 and a resonance means 9.

In the example of FIG. 6A to 6D the intake means 7 comprises an aerosolizer 65 which may be arranged to direct a spray of fluid comprising particles 3 into the chamber 5. The aerosolizer 65 may be arranged to direct a specified amount of fluid comprising particles 3 into the chamber 5. The particles 3 could be solid particles or liquid particles.

In the example of FIGS. 6A to 6D the aerosolizer 65 is provided within a reservoir 67. The reservoir 67 provides means for storing the product 69. The product 69 may comprise a medicinal product. The medicinal product may be for treating a condition of the respiratory system of a user 61.

A conduit 26 extends between the reservoir 67 and the chamber 5. The conduit 26 enables fluid and particles 3 from the aerosolizer 65 to be directed into the chamber 5. The conduit 26 also enables any particles 3 that are not affected by the acoustic standing waves in the chamber 5 to drop back into the reservoir 67.

In the example of FIGS. 6A to 6D the resonance means 9 comprises a speaker 60. The speaker 60 may be arranged to generate ultrasonic waves to resonate the chamber 5 and provide the standing acoustic pressure wave. In the example of FIGS. 6A to 6D the speaker 60 is provided at a first end of the chamber 5. The opposite end of the chamber comprises a sealing means 63.

The sealing means 63 may comprise a cap or any other suitable means for sealing the chamber 5. The sealing means 63 may be removable so that fluid and particles in the chamber 5 can be removed.

In the example of FIG. 6A the apparatus 1 is arranged ready for use as a drug delivery system. The apparatus 1 is arranged with the sealing means 63 sealing the end of the chamber 5. The apparatus 1 is positioned so that the end of the chamber 5 comprising the sealing means 63 is positioned adjacent to the mouth of a user 61.

In FIG. 6B the intake means 7 have provided the fluid and particles 3 into the chamber 5. This is provided as a spray into the chamber 5. The sealing means 63 remains in the closed position so that the fluid and particles 3 are enclosed within the chamber 5.

In FIG. 6C the resonance means 9 have been activated to provide the standing acoustic pressure wave. This has caused a plurality of particles 3 to collect at the node 11 of the chamber 5. Any particles 3 that have a size that are not affected by the standing acoustic pressure wave will drop back into the reservoir 67 so that only particles having a diameter above a threshold will be collected at the node 11. The threshold of the particle size will be determined by the frequency used to excite the chamber 5.

The sealing means 63 still remain in the closed position so that the fluid and particles 3 are still enclosed within the chamber 5.

In FIG. 6D the sealing means 63 are removed from the end of the chamber 5 so that the particles 3 can be inhaled by the user 61. In this example the open end of the chamber 5 may be placed inside, or adjacent to, the user's mouth to enable the user to inhale the particles 3.

Before the apparatus 1 is used the user 61 and/or a medical practitioner may have selected the size of particles that are needed. For instance the user 61 or medical practitioner may have indicated the part of the respiratory system that requires the medicament and in response the apparatus 1 may be arranged to collect particles 3 having a corresponding size. The particles 3 of the corresponding size may be obtained by exciting the chamber 5 with a correspond frequency. In such examples a the apparatus 1 may comprise a user interface which enable the user 61 to select the size of particles that are need. The apparatus 1 may also comprise controlling circuitry arrange to control the resonance means 9 to generate a standing wave so as to provide particles 3 of the selected size.

In the examples of FIG. 6A to 6D the chamber comprises a sealing means 63. In other examples the sealing means 63 need not be provided and the chamber 5 could be open ended.

In some examples a plurality of different medicaments could be provided in the reservoir. The different medicaments could be provided to the user 61 by exciting the chamber 3 at different resonant frequencies so that particles 3 having different sizes are collected at the nodes 11.

In the examples of FIGS. 6A to 6D the apparatus 1 does not comprise any detection means 24. In other examples the drug delivery system could comprise one or more detection means 24. These could be arranged to ensure that particles 3 of the correct size are being delivered to the user 61.

Figure 7:
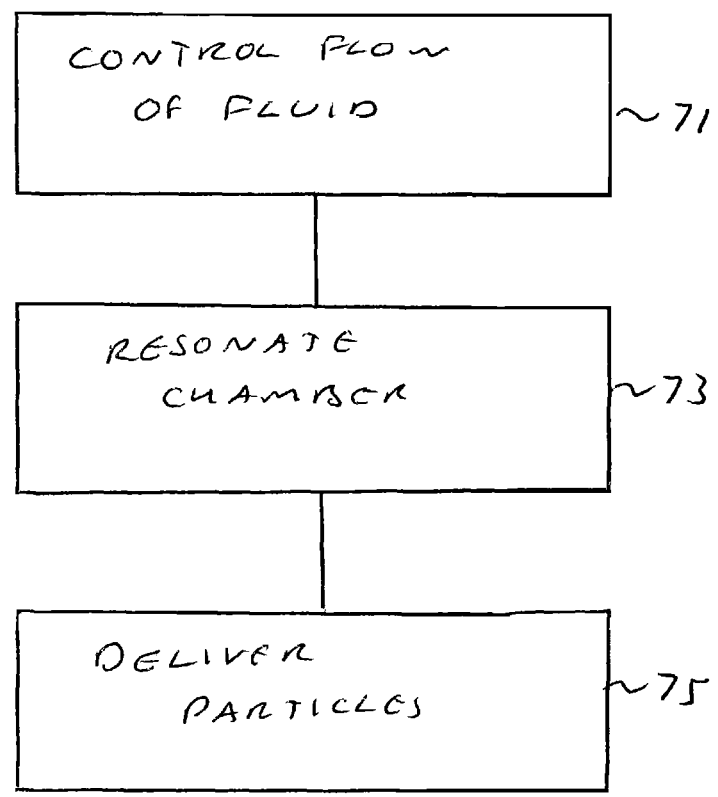

The example apparatus 1 shown in FIGS. 6A to 6D could be used to treat a medical condition of a subject. The medical condition could be a condition of the respiratory system or any other medical condition. FIG. 7 shows an example method of using the apparatus 1 to treat a medical condition.

The method comprises, at block 71, controlling a flow of fluid into the chamber 5 of the apparatus 1, wherein the fluid comprises particles 3. The particles 3 could comprise a medicinal product. The particles 3 could comprise solid particles and/or liquid particles.

At block 73 the method comprises resonating the chamber 5 to provide an acoustic standing wave within the chamber 5. The frequency of the standing wave is selected to cause particles 3 above a specific size to collect at a node 11 of the standing wave. Different frequencies of the standing wave will cause particles 3 of different sizes to collect at the nodes 11. The frequency of the standing wave may therefore be selected to control the size of particles 3 collected at the node 11 of the standing wave.

At block 75 the method comprises delivering the particles 3 collected at the node to a subject. Delivering the particles 3 to the subject could comprise removing the sealing means 63 from the end of the chamber 5 and enabling a subject to inhale the contents of the chamber 5.

Examples of the disclosure provide an apparatus 1 which enables 3 particles of different sizes to be collected at a particular location within a chamber 3. The number of particles at each size, or the volume of particles 3 at each size can then be determined. In some examples the chemistry of the particles 3 could also be analysed. This information could then be used to design filters or other protective devices so as to prevent the particles 3 from damaging electronic components or other goods.

In some examples the collected particles 3 could then be provided for a particular purpose where particles 3 having a particular size are required. For example they could be provided as a medicament within a drug delivery system.

In the description above the term coupled means operationally coupled. Any number or combination of intervening elements can exist between coupled components, including no intervening elements.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples.

Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus, comprising:
   a chamber;
   an intake device configured to control a flow of fluid into the chamber, wherein the fluid comprises particles; and
   a first resonance device located at an end of the chamber and configured to resonate the chamber to provide an acoustic standing wave within the chamber,
   wherein a frequency of the standing wave is selected to cause particles above a specific size to collect at a node of the standing wave,
   wherein the intake device comprises a conduit and a second resonance device located at an open end of the conduit,
   wherein the conduit extends perpendicularly from a side of the chamber and is in direct fluid connection with the chamber at the side of the chamber, and
   wherein the conduit comprises an absorptive material disposed between the second resonance device and the chamber.

2. The apparatus as claimed in claim 1 wherein the particles are suspended within the fluid.

3. The apparatus as claimed claim 1, wherein the fluid comprises a gas.

4. The apparatus as claimed in claim 1, wherein the intake device further comprises at least one of a fan, a heating element, an aerosolizer.

5. The apparatus as claimed in claim 1, wherein the first resonance device and the second resonance device each comprise one or more piezoelectric transducers.

6. The apparatus as claimed in claim 1, comprising a detection device configured to detect the particles collected at the node of the standing wave.

7. The apparatus as claimed in claim 6, wherein the detection device comprises one or more light sources and one or more photodetectors.

8. The apparatus as claimed in claim 7, wherein the one or more light sources are arranged to provide light of a plurality of different wavelengths and the one or more photodetectors are arranged to enable the response of the particles to the different wavelengths of light to be detected.

9. The apparatus as claimed in claim 6, wherein the detection device comprises an imaging device.

10. The apparatus as claimed in claim 1, wherein the chamber comprises a sealing device configured to seal the chamber, wherein the sealing device is configured to be removed to enable the fluid and particles to be removed from the chamber.

11. The apparatus as claimed in claim 1, wherein the particles above a specific size have a diameter above a specific length and/or a mass above a specific mass.

12. The apparatus as claimed in claim 1, wherein the particles comprise one or more droplets.

13. A method, comprising:

controlling a flow of fluid from a conduit into a chamber, wherein the fluid comprises particles; and resonating the chamber with a first resonance device located at an end of the chamber to provide an acoustic standing wave within the chamber, wherein a frequency of the standing wave is selected to cause particles above a specific size to collect at a node of the standing wave, wherein the controlling of the flow of fluid from the conduit into the chamber comprises controlling the flow with an intake device comprising a second resonance device, wherein the controlling of the flow of fluid from the conduit into the chamber comprises controlling the fluid to flow perpendicularly in the conduit from the flow of fluid in the chamber, and through a side opening of the chamber, and wherein the controlling of the flow of fluid from the conduit into the chamber comprises controlling the fluid to flow around an absorptive material disposed between the second resonance device and the chamber.

14. The method according to claim 13, wherein the particles are suspended within the fluid.

15. The method according to claim 13, wherein the fluid comprises a gas.

16. The method according to claim 13, wherein the intake device further comprises at least one of a fan, a heating element, and an aerosolizer.

17. The method according to claim 13, wherein the first resonance device and the second resonance device each comprise one or more piezoelectric transducers.

18. The method of claim 13, further comprising detecting the particles collected at the node of the standing wave.

* * * * *